(12) United States Patent
Tomita

(10) Patent No.: US 6,325,793 B1
(45) Date of Patent: *Dec. 4, 2001

(54) LASER TREATMENT APPARATUS

(75) Inventor: Seiki Tomita, Gamagori (JP)

(73) Assignee: Nidek Co., Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/294,895

(22) Filed: Apr. 20, 1999

(30) Foreign Application Priority Data

Apr. 30, 1998 (JP) .................................................. 10-121021

(51) Int. Cl.$^7$ .................................................... A61B 18/18
(52) U.S. Cl. ........................ 606/4; 606/5; 606/6; 606/10; 607/89
(58) Field of Search .............................. 606/4–6, 10–12; 607/88; 128/898

(56) References Cited

U.S. PATENT DOCUMENTS

| | | | |
|---|---|---|---|
| 5,098,426 | * | 3/1992 | Sklar et al. ............................... 606/5 |
| 5,147,349 | * | 9/1992 | Johnson et al. ........................... 606/4 |
| 5,395,356 | * | 3/1995 | King et al. ................................ 606/4 |
| 5,439,462 | * | 8/1995 | Bile et al. ................................. 606/6 |
| 5,445,633 | * | 8/1995 | Nakamura et al. ....................... 606/5 |
| 5,800,424 | * | 9/1998 | Sumiya .................................... 606/4 |
| 5,906,608 | * | 5/1999 | Sumiya et al. ........................... 606/5 |

FOREIGN PATENT DOCUMENTS

| | | |
|---|---|---|
| 0 729 734 | 9/1996 | (EP) . |
| 8-229064 | 9/1996 | (JP) . |

OTHER PUBLICATIONS

"VISULAS YAG II" plus "Intelligence and precision in a standard–setting system", Ophthalmic Instruments from Carl Zeiss (8 pages); Publication No. YPB Rev. A 10M 1098.

* cited by examiner

Primary Examiner—Linda C. M. Dvorak
Assistant Examiner—Ahmed Farah
(74) Attorney, Agent, or Firm—Finnegan, Henderson, Farabow, Garrett & Dunner, L.L.P.

(57) ABSTRACT

A laser treatment apparatus for treating an affected part to irradiate it with a laser beam. The apparatus includes a laser source which emits a treatment laser beam, a light delivery optical system for delivering the laser beam from the laser source to the affected part, an adjustment device for shifting a focal position of the laser beam to be applied to the affected part in an optical axis direction with respect to a focal position of an aiming light, an input device for inputting a signal for commanding the adjustment device to adjust the focal position of the laser beam or a signal for confirmation of a condition of the focal position which has been adjusted by the adjustment device, an instruction device for inputting an instruction signal to apply the laser beam to the affected part, and a warning device for providing warning to an operator in response to the instruction signal input with the instruction device, when neither the adjustment command signal nor the confirmation signal has been input.

18 Claims, 7 Drawing Sheets

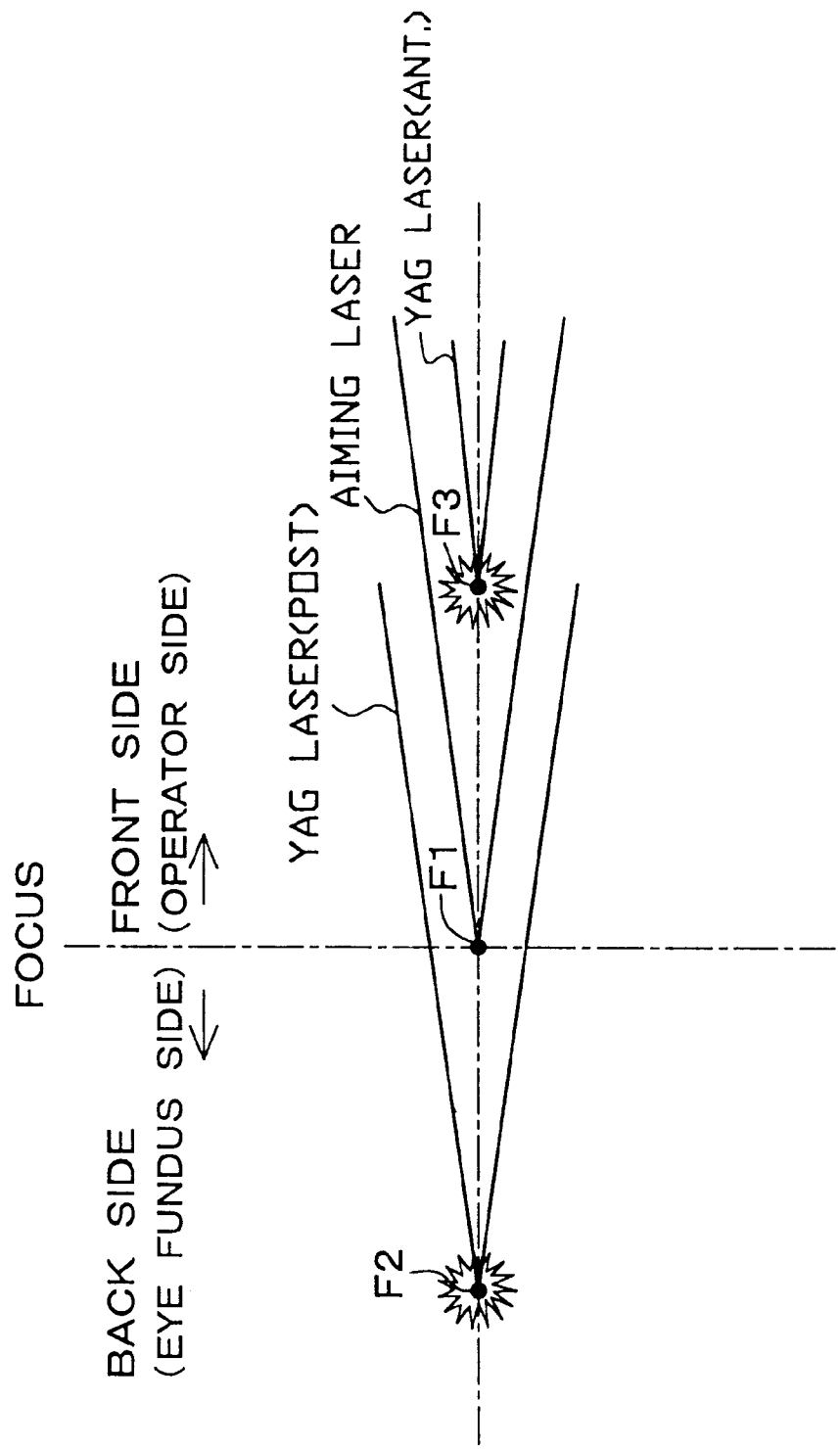

LASER TREATMENT APPARATUS

BACKGROUND OF THE INVENTION

1. Field of the Invention

The present invention relates to a laser treatment apparatus for treating an affected part by irradiating it with a laser beam for treatment.

2. Description of Related Art

In laser treatment apparatus which is represented by a YAG laser used in the field of ophthalmology, the focal position of a laser beam for treatment is made to shift for an aiming light in an optical axis direction when an operation of incising posterior capsule for after cataract treatment or iris for glaucoma treatment is carried out, in order to reduce the effect by the impact of the treatment laser beam to an intraocular lens and to raise the efficiency of incising. The YAG laser is constructed to concentrate the energy of the laser beam on the focal point, whereby to cut off the tissue irradiated by the laser beam.

FIG. 7 shows the case that the focal position of the treatment laser beam is shifted in the optical axis, in which the focal position of an aiming light is located at the position F1. In this case, there are two ways to shift the focal position of the YAG laser beam, namely, one way is to shift the focal position to a back side (an eye fundus side) as indicated by a position F2 and another is to shift the same to a front side (an operator side) as indicated by a position F3.

The way to shift the focal position to the back side up to the position F2 is performed when an object which requires not to be injured by the YAG laser beam, such as an intraocular lens, exists on the front side. In the after cataract, it is necessary to incise opaque posterior capsule by the treatment YAG laser beam. However, intraocular lens has been inserted on the operator side, and the focal position of the YAG laser beam is shifted to the back side in order to prevent the laser beam from injuring the lens in error.

The way to shift the focal position to the front side up to the position F3 is performed when an object which requires not to be injured by the YAG laser beam exists on the back side.

In the above laser treatment, the setting of the focal shift position of the treatment laser beam is often changed according to patient eye cases and for each person.

However, in the case that the laser treatment apparatus is used for a patient's eye different from an eye that was treated with the identical apparatus at the last time, in particular, in the case that the identical apparatus is used by plural operators, the confirmation or reset of the focal shift position for the laser beam are often forgotten, and the laser irradiation might be carried out using the focal shift position set at the last time use (when the other operator used, and other cases). Therefore, the purposed treatment effect may not be obtained. There is also the fear that the intraocular lens may be injured in error in the operation of the after cataract, when the focal position of the YAG laser beam is located at the position corresponding to that of the aiming light or on the front side.

To avoid the above problem, under present circumstances, the means such as specification in instruction manuals and attachment of attention labels to the apparatus are taken. However, those are not always reliable.

SUMMARY OF THE INVENTION

The present invention has been made in view of the above circumstances and has an object to overcome the above problems and to provide a laser treatment apparatus which can prevent that irradiation of a treatment laser beam is carried out, using the current setting of a focal position, which is different from an intended one.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for treating an affected part by irradiating it with a laser beam, the apparatus including a laser source which emits a treatment laser beam, a light delivery optical system for delivering the laser beam emitted from the laser source to the affected part to irradiate it, an adjustment device for shifting a focal position of the laser beam to be applied to the affected part in a direction of an optical axis with respect to a focal position of an aiming light, an input device for inputting a signal for commanding the adjustment device to adjust the focal position of the laser beam or a signal for confirmation of a state of the focal position which has been adjusted by the adjustment device, an instruction device for inputting an instruction signal to enable laser irradiation to the affected part, and a warning device for providing warning to an operator in response to the instruction signal input with the instruction device if neither the adjustment command signal nor the confirmation signal has been input.

In the above apparatus, when an operator operates the instruction device to apply the laser beam to the affected part, the warning device provides the warning to prompt the operator to confirm the focal position for safety if neither the focus adjustment signal nor the focus confirmation signal for the laser beam has been input. In response to the warning, the operator checks the focal position and, if it is different from an intended position, adjusts the focal position with the adjustment device, or, if it agrees with the intended position, inputs a confirmation signal with the input device.

Subsequently, the operator inputs the instruction signal with the instruction device, and the laser irradiation is made ready to start to irradiate the affected part.

According to a second aspect of the present invention, there is provided a laser treatment apparatus for treating an affected part by irradiating it with a laser beam, the apparatus including, a laser source which emits a treatment laser beam, a light delivery optical system for delivering the laser beam emitted from the laser source to the affected part to irradiate it, an adjustment device for shifting a focal position of the laser beam to be applied to the affected part in a direction of an optical axis with respect to a focal position of an aiming light, an input device for inputting a signal for commanding the adjustment device to adjust the focal position of the laser beam or a signal for confirmation of a state of the focal position which has been adjusted by the adjustment device, an instruction device for inputting an instruction signal to enable laser irradiation to the affected part, and an irradiation restriction device which enables the laser irradiation when the instruction signal is input with the instruction device if at least one of the adjustment command signal and the confirmation signal has been input, and disables the laser irradiation when the instruction signal is input if neither the adjustment command signal nor the confirmation signal has been input.

In the above apparatus, when an operator operates the instruction device to apply the laser beam to the affected part, the irradiation restriction device forbids the laser irradiation in order to ensure safety if neither the focus adjustment signal nor the focus confirmation signal has been input. When the operator checks the focal position and adjusts it with the adjustment device if the focal position is different from the intended one or inputs the confirmation signal if it agrees with the intended one.

Subsequently, the operator inputs the instruction signal with the instruction device and the laser beam is made ready to emit, irradiating the affected part.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 7 is an explanatory view of the focal position of a treatment laser beam.

DETAILED DESCRIPTION OF THE PREFERRED EMBODIMENTS

Figure 1:
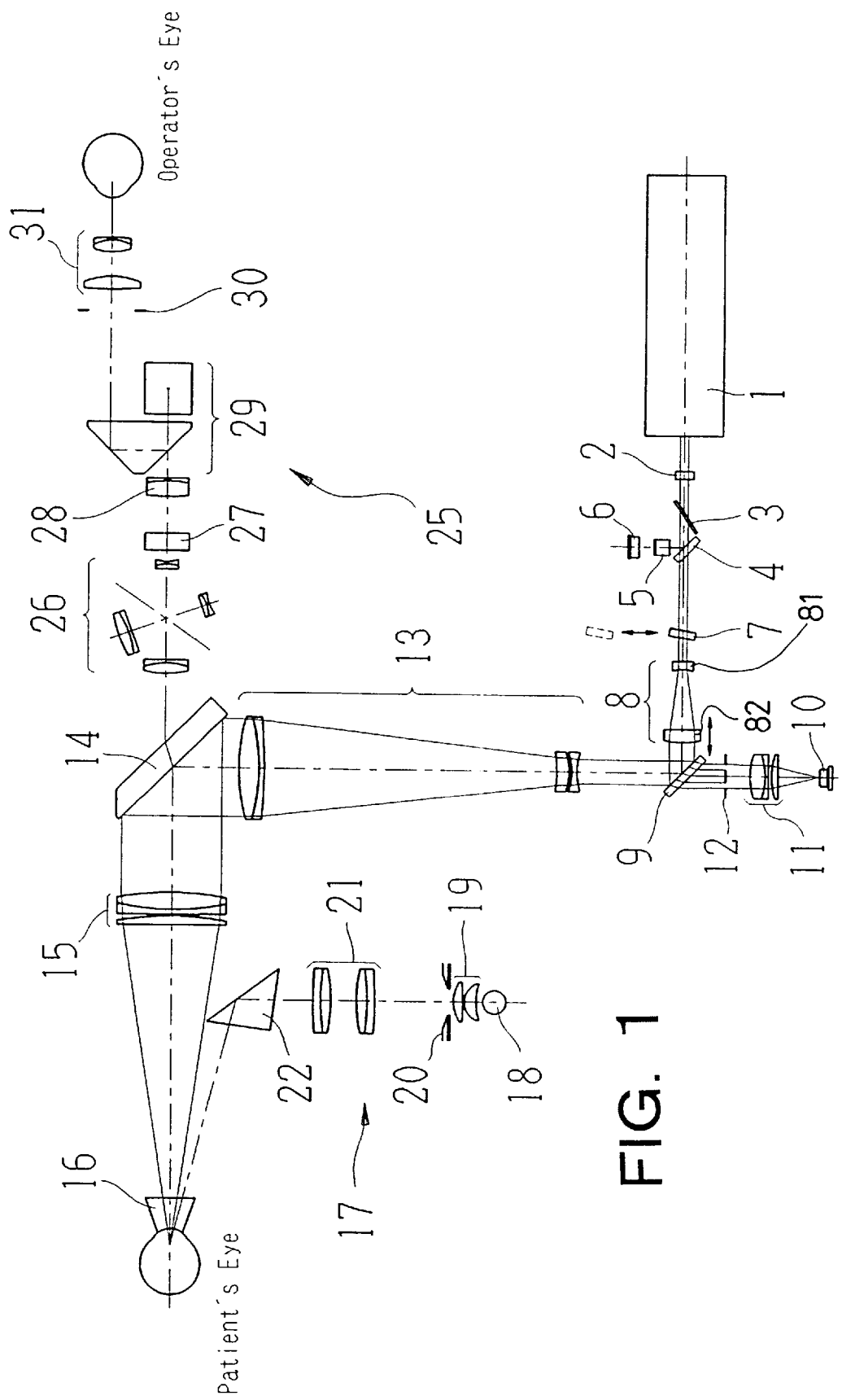
FIG. 1 is a schematic diagram of an optical system of a laser treatment apparatus in an embodiment according to the present invention.

A detailed description of a preferred embodiment of a laser treatment apparatus embodying the present invention will now be given referring to the accompanying drawings.

Reference number 1 indicates a laser source which emits a treatment laser beam (simply referred to as a laser beam hereinafter). For this laser source 1 is used an Nd:YAG laser which can emit a laser beam at a dominant wavelength of 1064 nm. Reference number 2 indicates a half-wave plate which rotates the polarizing direction of a laser beam. Reference number 3 indicates a polarizing plate disposed at an angle of polarization. By rotation of the half-wave plate 2 with aid of an adjustment knob not illustrated, in combination of the polarizing plate 3, the energy level of the laser beam is regulated. The laser beam passed through the polarizing plate 3 is partially reflected by a beam splitter 4. The reflected part of the laser beam is introduced into a beam detection sensor 6 via an attenuator 5. The sensor 6 then detects the output level of the laser beam.

The laser beam passed through the beam splitter 4 is led to a dichroic mirror 9 through a beam shutter 7 and a focal shift lens 8. The dichroic mirror 9 makes the laser beam to be coaxial with an aiming light. The focal shift lens 8 is moved in an optical axis direction through a lens movement mechanism 43 by the operation of a focal shift adjustment knob 41. With movement of the focal shift lens 8, a focal position of the laser beam is shifted with respect to the focal position of the aiming light in an affected part of a patient's eye.

Figure 4:
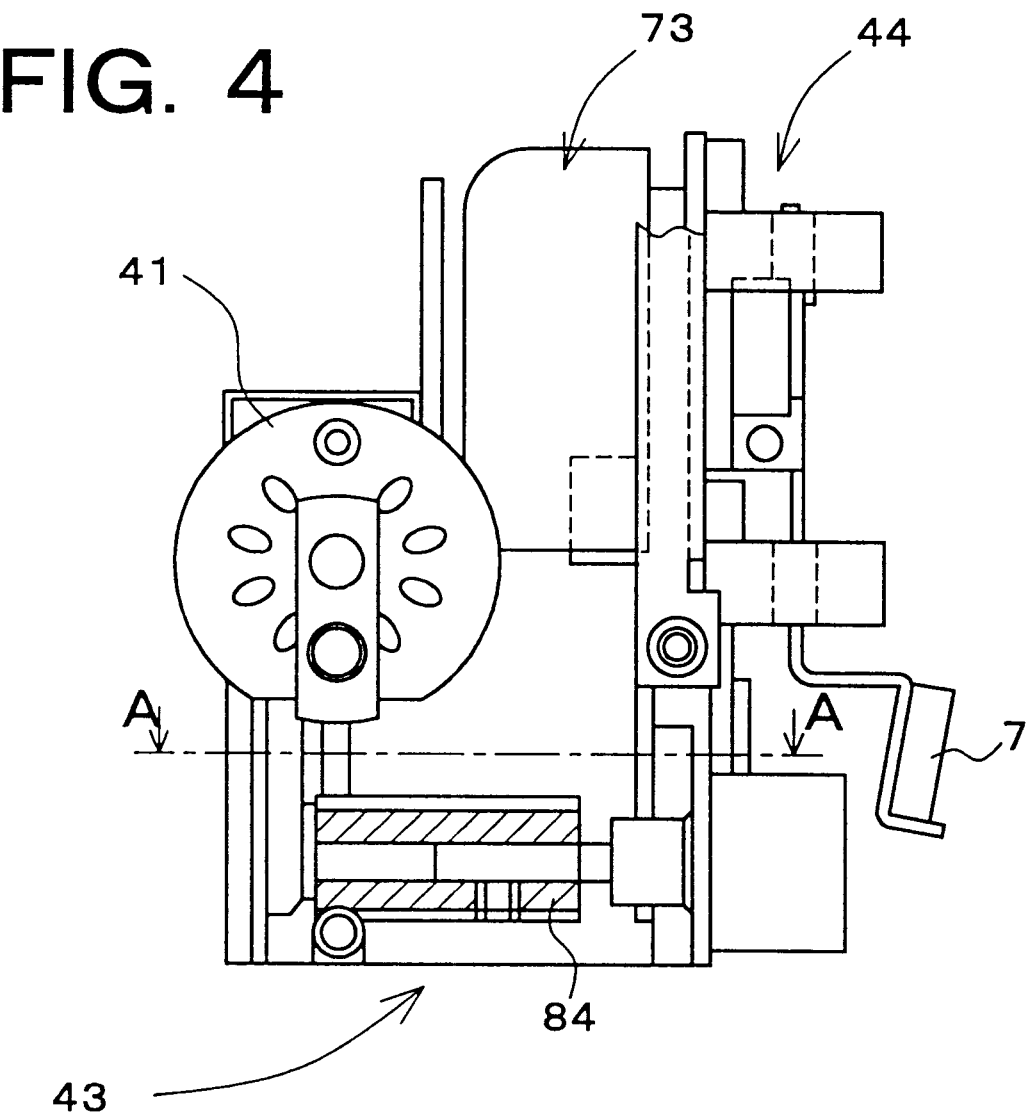
FIG. 4 is a front view of a focal shift lens and a beam shutter of the laser treatment apparatus.
Figure 5:
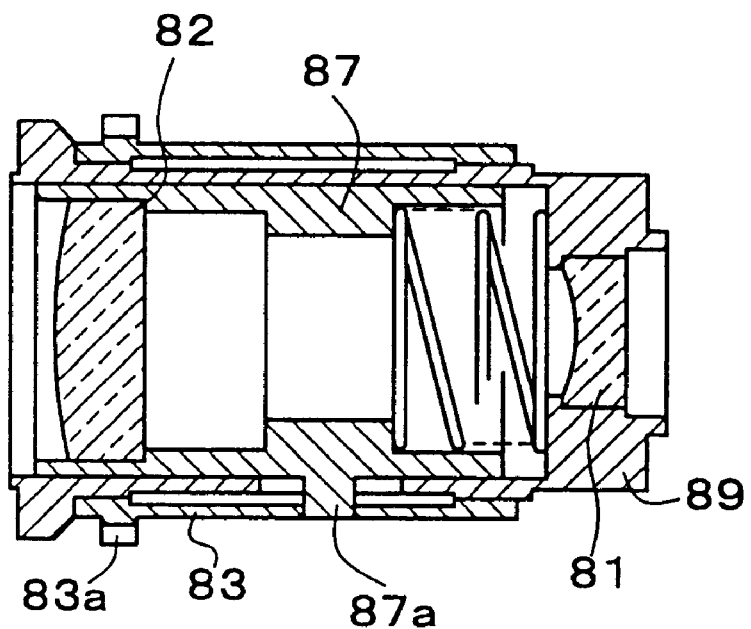
FIG. 5 is a cross sectional view taken along the line A-A in FIG. 4, showing a structure of the focal shift lens.
Figure 6:
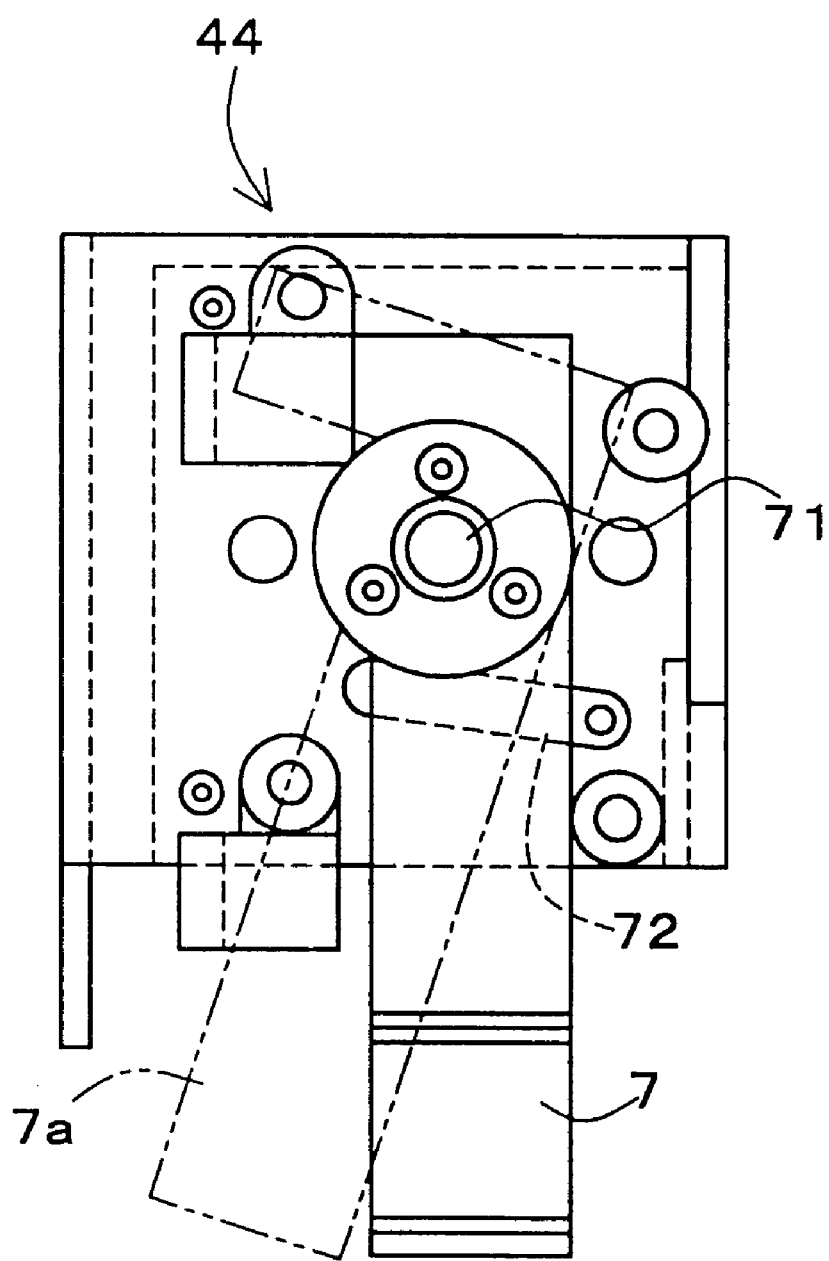
FIG. 6 is a side view of a shutter movement mechanism of the laser treatment apparatus.

FIG. 4 shows a front view of an assembly of the lens movement mechanism 43 and a shutter movement mechanism 44. FIG. 5 shows a cross sectional view of the lens movement mechanism 43 take along the line A—A of FIG. 4. FIG. 6 shows a right side view of the shutter movement mechanism 44 of FIG. 4.

As shown in FIG. 5, a mount 89 fixedly holds therein a concave lens 81. A rotary cam 83 is rotatably mounted on the outer periphery of the mount 89 with a grooved cam. A lens holder 87 is slidably held in the rotary cam 83. The lens holder 87 is provided with a convex portion 87a formed on the outer periphery of the holder 87. This convex portion 87a is fitted in the grooved cam of the rotary cam 83. In the lens holder 87, a convex lens 82 is aligned coaxially with the concave lens 81 on the identical optical axis.

The focal shift adjustment knob 41 is rotatably retained in the mount 89. The shaft of the knob 41 has a gear which is engaged with a gear 83a formed on the outer periphery of the rotary cam 83. The gear 83a is connected to an adjustment detection sensor 42, such as a potentiometer, for detecting the location of the convex lens 82 through a screw gear 84.

As shown in FIG. 6, on the other hand, the shutter movement mechanism 44 is constructed such that the beam shutter 7 is rotatably attached to an output shaft 71 of a solenoid 73 for driving the shutter 7. The imaginary line 7a shows the state that the optical path is opened due to the movement of the beam shutter 7. The shutter 7 is always urged by a spring 72 in the direction where the optical path is interrupted by the shutter. Upon applying the electric current to the solenoid 73, the beam shutter 7 is moved to the position indicated by the imaginary line 7a, allowing the YAG laser beam to pass along the optical path.

Reference number 10 is a light source which emits an aiming light, and a visible semiconductor laser is used therefor. The aiming light emitted by the light source 10 is made to be parallel luminous flux by a collimator lens 11, separated into two luminous flux by an aperture 12 having two openings, and then made to be coaxial with the laser beam by the dichroic mirror 9. The aiming light and the laser light are widened by a beam expander 13, reflected by a dichroic mirror 14, and introduced into the patient's eye through an objective lens 15 and a contact lens 16.

Reference numeral 17 indicates an illumination optical system for slit-illuminating the patient's eye. In the optical system 17, the illumination light emitted by a light source 18 passes through a condenser lens 19, a slit aperture 20, and a projection lens 21, and the light is deflected by a prism 22 toward the patient's eye. The eye is thus illuminated.

Reference number 25 indicates a binocular observation optical system for observing the patient's eye. This optical system 25 includes a magnification varying optical system 26, an operator protecting filter 27, an objective lens 28, an erect prism group 29, a visual field diaphragm 30, and eyepieces 31. For the illumination optical system 17 and the observation optical system 25, well-known systems can be used, and the detailed explanation thereof is omitted.

Figure 2:
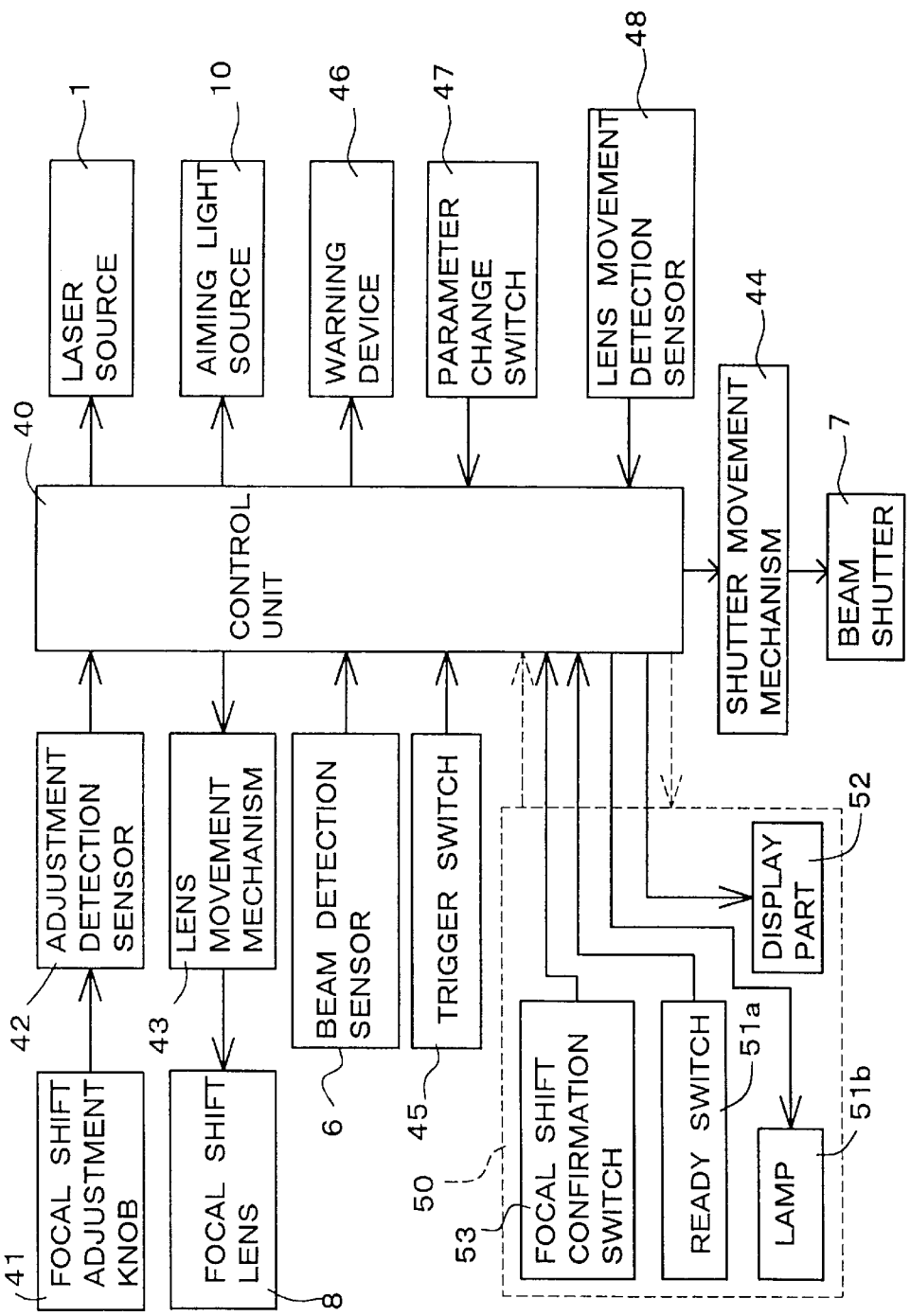
FIG. 2 is a schematic diagram of a control system of the laser treatment apparatus.

FIG. 2 is a structural view of a control system of the laser treatment apparatus in the embodiment, in which only essential parts are illustrated. Reference number 40 indicates a control unit. As the focal shift adjustment knob 41 for moving the focal shift lens 8 is rotated, the convex lens 82 is moved backward or forward along the optical axis. The laser beam being widened by the concave lens 81, when the convex lens 82 is moved along the optical axis, the focal position of the YAG laser beam can be shifted back or forth with respect to the focal position of the aiming light.

The control unit 40 detects the direction and the amount of movement of the focal shift lens 8 in response to a detection signal from the sensor 42.

In the present embodiment, the focal shift adjustment knob 41 and the lens movement mechanism 43 are mechanically linked. It may also be configured such that a motor is used in the lens movement mechanism 43, the output of the knob 41 is detected by an extra potentiometer, and the motor of the mechanism 43 is driven based on the detection value.

The control unit 40 controls the shutter movement mechanism 44 to move the shutter 7 into or away from the optical path. For the lens movement mechanism 43 and the shutter movement mechanism 44, well-known mechanisms such as a motor, a slid mechanism, etc. can be used. Reference number 45 indicates a trigger switch for generating a trigger signal to apply the laser beam to the affected part. The trigger switch 45 is provided in a top of a joystick or a foot switch, not illustrated. Reference number 46 indicates a warning device for prompting the operator to check the focal shift state. Reference number 47 indicates a parameter change switch for changing operational modes and the like of the apparatus.

Figure 3:
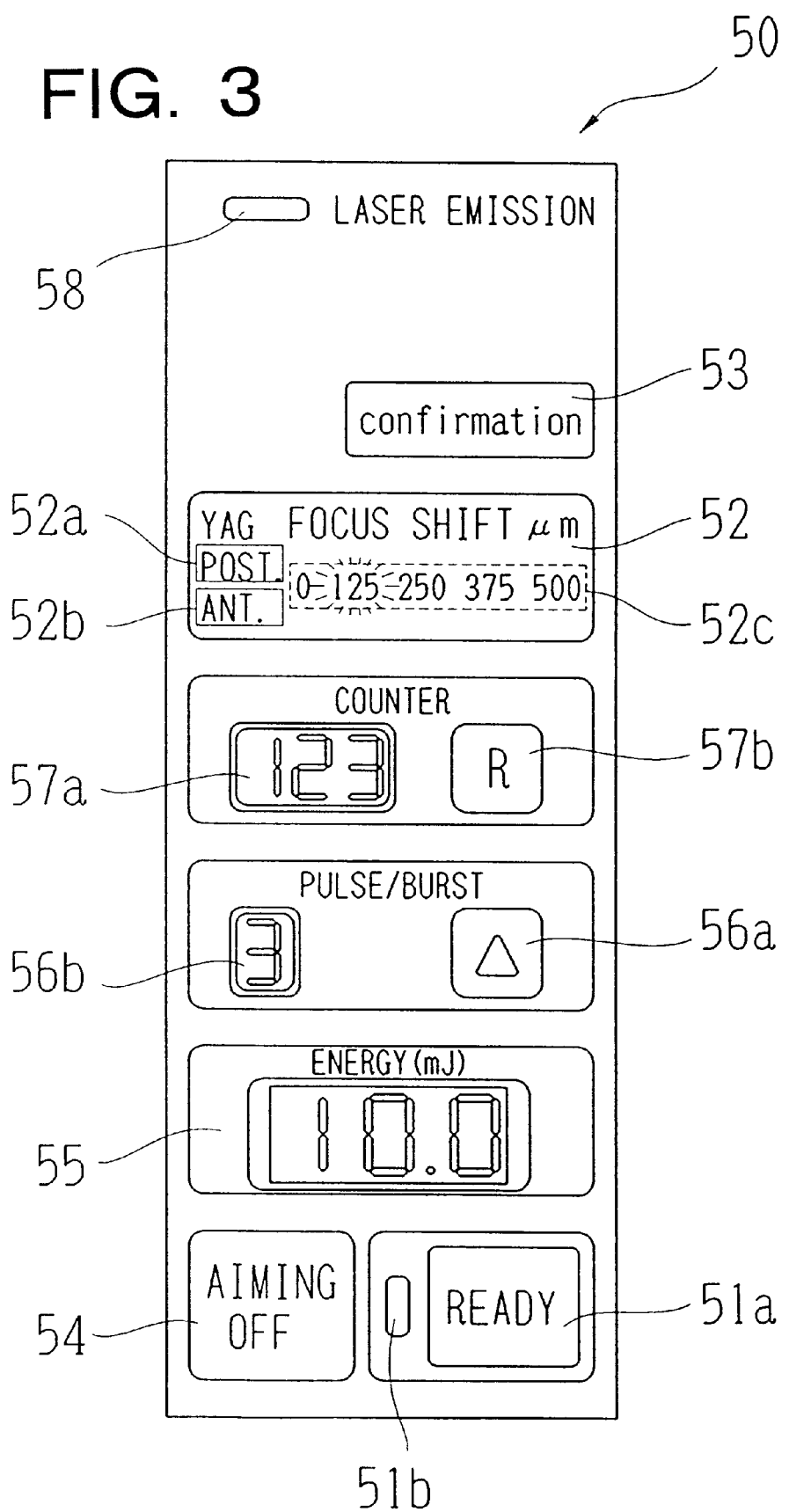
FIG. 3 is an arrangement diagram of a control panel of the laser treatment apparatus.

Reference number 50 indicates a control panel, on which various input switches and display parts as shown in FIG. 3.

Reference number 51a is a READY switch for setting whether the apparatus is put in a ready state for laser irradiation (specifically, which is the state that the laser beam can be emitted by a push of the trigger switch 45). In response to the ON/OFF state of the switch 51a, a lamp 51b disposed at a side of the switch 51a is turned on/off. Upon turning on the READY switch 51a, a signal is transmitted to the control unit 40, which controls the shutter movement mechanism 44 to move the shutter 7 away from the optical path of the laser beam. Accordingly, the laser beam is ready to emit.

Reference number 52 is a display part for displaying a state of the focal shift position of the laser beam with respect to the focal position of the aiming light. When the focal shift position of the laser beam is set on a back side (the eye fundus side) with respect to the focal position of the aiming light, a display 52a of "POST." lights on. When it is set on a front side (the operator side), alternatively, a display 52b of "ANT." lights on. The focal position of the laser beam is able to be set within a range of 0 to 500 µm in each direction by the operation of the adjustment knob 41. The operator can know the shift position by any one lightened numerical value of 0, 125, 250, 375, and 500. The shift position may be displayed by a continuously variable value on the display part. The focal shift position of the laser beam, namely, the shift direction and amount of the laser beam with respect to the focal position of the aiming light, displayed on the display part 52 is calculated in the control unit 40 based on the adjustment direction and adjustment amount from a standard position (where the focal position of the laser beam agrees with that of the aiming light, namely, the shift amount equals to zero) which is detected by the sensor 42. The control unit 40 controls the display part 52 based on the calculated result. It is to be noted that a lens movement detection sensor 48, such as a potentiometer, an encoder, etc., for detecting the movement direction and movement amount of the focal shift lens 8 may be additionally provided such that the display part 52 displays the focal shift position based on the movement direction and amount detected by the sensor 48. Also, a pulse motor may be used for the lens movement mechanism 43 such that the display part displays the movement direction and amount based on the number of pulses.

Reference number 53 indicates a focal shift confirmation switch, which is pressed when no operation of the adjustment knob 41 is required because the current focal position, which was set at the last time use, is used.

For other switches and display parts, there are provided a lamp 54 for indicating lights-on and lights-off conditions of the aiming light, an energy display part 55 for indicating the set laser energy intensity, a switch 56a for setting the number of laser irradiation in response to one trigger signal, a display part 56b for displaying the set laser irradiation number, a display part 57a for displaying the accumulative number of the laser irradiation, a reset switch 57b for resetting the display part 57a, and a lamp 58 for lightning up during the power-on period.

The operation of the laser treatment apparatus constructed as above will be explained below. In the present embodiment, explanation is made on an example of the laser treatment performed for incising posterior capsule in order to treat after cataract.

The operator operates the switches on the control panel 50 and the various setting knobs not illustrated, to set the irradiation conditions including the laser output level, the number of irradiation pulses, and others according to the treatment purpose for the patient's eye. Confirming the current focal position displayed on the display part 52, the operator sets a desired value by turning the adjustment knob 41 if changes are needed. If the focal position set at the last time is used as it is, needing no change, the confirmation switch 53 is depressed.

After the completion of prior preparations, the patient's eye is placed at a predetermined position. The operator manipulates the joystick for moving the optical system in order to carry out rough positioning of the optical system with respect to the patient's eye illuminated by the illumination optical system 17. Subsequently, after applying the contact lens 16 onto the patient's eye, the operator further manipulates the joystick while observing the patient's eye through the observation optical system 25 to further move the optical system. Rough adjustment of the aiming light with respect to the patient's eye is thus made.

After the above steps, the READY switch 51a is turned on, when the laser irradiation is ready to start. If the manipulation of the adjustment knob 41 or the confirmation switch 53 has not been carried out beforehand, that is to say, if either operational signal, namely, the detection signal from the sensor 42 or the input signal by the confirmation switch 53, has not been entered, the control unit 40 forbids the transition of the apparatus to the state ready for the laser irradiation. This is done by keeping the beam shutter 7 placed in the optical path of the laser beam. The control unit 40 simultaneously causes the warning device 46 to provide warning such as a warning sound and/or a warning display to the operator. For the warning display, for example, the display of the confirmation switch 53 is lightened up. This makes it possible to avoid that the laser irradiation is carried out using the current focal position which is different from that the operator intends, even when the operator forgot to confirm or reset the focal position.

When the laser beam is made ready to emit by turning on the READY switch 51a (then, the manipulation of the adjustment knob 41 or the depression of the confirmation switch 53 has been carried out beforehand), the operator operates the joystick to minutely adjust the range of the aiming light in the affected part of the posterior capsule to be incised. The focal position of the aiming light can be adjusted to the affected part by adjusting such that the aiming light separated into two luminous flux may overlap with each other at a point. The focal position of the laser beam is then placed on the back side or the front side by the setting by means of the adjustment knob 41 with respect to the focal position of the aiming light. In the case of incising the posterior capsule, the focal position of the laser beam is set to be on the back side in order to avoid the impact on the intraocular lens inserted.

Upon completion of the adjustment of the aiming light, the operator depressed the trigger switch 45 to enter the trigger signal. The control unit 40 causes the light source 1 to emit the laser beam, which is delivered to the affected part through the optical system, irradiating the affected part. The plasma then generates in the focus and causes the tissue destruction on the back side thereof. Thus, the posterior capsule incision is carried out without increasing the effect on the intraocular lens inserted instead of a crystalline lens. After the laser irradiation is finished, the switch 51a is turned off to prevent the laser irradiation from starting by misoperation of the trigger switch 45.

In the present embodiment, the adjustment knob 41 is turned to set a desired value for the focal shift position if its change is needed, alternatively, the confirmation switch 53 is depressed if the change is not needed. Without either operation, the laser irradiation is not enabled even if the switch 51a is turned on. In this case, the warning device provides warning. This, however, may be changed as the following modification example.

For example, the parameter change switch 47 is used to change a mode. The safety mechanism is arranged to work only when the mode (standard mode) is changed to a restriction mode. Specifically, when the restriction mode is chosen, the irradiation of the laser beam is not enabled, that is to say, the shutter 7 is not removed from the optical path of the laser beam, even if the switch 51a is turned on unless the adjustment knob 41 has been turned or the confirmation switch 53 has been depressed. In this state, the warning device provides warning. On the other hand, the restriction mode is not chosen, the irradiation of the laser beam is enabled, that is to say, the shutter 7 is removed from the optical path when the switch 51a is turned on even if neither the adjustment knob 41 nor the confirmation switch 53 has been operated. When a single operator uses the apparatus, unless the restriction mode is chosen, no extra operation is needed and also unnecessary warning is not provided. When plural operators use the identical apparatus, if the restriction mode is chosen, this can prevents that the operators forget to confirm the focal shift position and change the setting.

The confirmation switch 53 may be omitted in the case that the mode is changed as in the above modification example. Specifically, it is arranged that the adjustment knob 41 is always manipulated by the operator when the restriction mode is chosen. Even if the focal shift position at this time is identical to that at the last time, the knob 41 is turned to adjust the focal shift position to the same one again. When the restriction mode is not chosen, the knob 41 is manipulated if the focal shift position is changed, while it may not be manipulated if the focal shift position is not changed, namely, in the case that the focal shift position set at the last time is used as it is.

The control unit 40 may be arranged to control the laser irradiation and the warning device based on the detection signal of the sensor 48, instead of the detection signal of the sensor 42, i.e., the operation signal of the adjustment knob 41.

In the present embodiment, furthermore, when the transition to the laser irradiation ready condition is forbidden, the shutter 7 is made to stay on the optical path of the laser beam. Alternatively, the laser source 1 itself may be controlled not to emit the laser beam.

The adjustment knob 41 may be used for a switch, whereby the control unit 40 may control the laser irradiation and the warning device based on the input signal from the switch. Similarly, the control unit 40 may control the movement of the focal shift lens 8 and the display of the display part 52 based on the input signal from the switch.

Furthermore, although the focal shift position of the laser beam is display on the display part 52 in the present embodiment, the display part 52 may be omitted if a scale is provided on the adjustment knob 41. For example, the above mentioned reference position, at which the focal position of the aiming light agrees with that of the laser beam, is made to be 0, and there is provided the scale of −125, −250, −375, −500 in the order when the focal position of the laser beam is set to the front side (operator side) for the focal position of the aiming light. There is provided, alternatively, the scale of +125, +250, +375, +500 in the order when the focal position of the laser beam is set to the back side (eye fundus side) for the focal position of the aiming light. The operator changes, referring to the scale of the adjustment knob 41, the setting of the focal position of the laser beam.

The present invention may be embodied in other specific forms without departing from the spirit or essential characteristics thereof.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus for treating an affected part of a patient's eye by irradiating the affected part with a laser beam, the apparatus comprising:

a laser source which emits a treatment laser beam;

light delivery optical system for delivering the laser beam emitted from the laser source to the affected part to irradiate the affected part with the laser beam;

an adjustment device, including input means for inputting an amount of focal shift, which independently shifts a focal position of the laser beam in a direction of an optical axis with respect to a focal position of an aiming light based on the input amount of focal shift;

a confirmation switch which is operator when an amount of focal shift does not need to be newly input based on confirmation of a state of the focal position of the laser beam or the amount of focal shift;

an instruction device which enables laser irradiation to the affected part based on input of a trigger signal; and a warning device which provides a warning to the operator when an irradiation condition of the laser beam or the trigger signal is input of the amount of focal shift nor operation of the confirmation switch has been detected.

2. The laser treatment apparatus according to claim 1, wherein the instruction device disables irradiation of the laser beam when the warning device provides the warning.

3. The laser treatment apparatus according to claim 1, wherein the instruction device enables irradiation of the laser beam when the irradiation condition and the trigger signal is input if the input of the amount of focal shift or the operation of the confirmation switch has been detected, and disables the laser irradiation when the irradiation condition or the trigger signal is input if neither the input of the amount of focal shift nor the operation of the confirmation switch has been detected.

4. The laser treatment apparatus according to claim 3 further comprising a shutter which is movable into or away from an optical path of the laser beam, wherein the instruction device controls movement of the shutter.

5. The laser treatment apparatus according to claim 1, wherein the adjustment device includes a focal shift lens disposed in the light delivery optical system,
the input means includes an operation device for moving the focal shift lens along the optical axis of the light delivery optical system, and
the input of the amount of focal shift is detected based on detection of movement of the focal shift lens or an operation signal which is input with the operation device.

6. The laser treatment apparatus according to claim 1, wherein the adjustment device includes a focal shift lens disposed in the light delivery optical system and a movement device which moves the focal shift lens along the optical axis of the light delivery optical system,
the input means includes a movement input device for inputting a movement amount of the focal shift lens to be moved by the movement device, and
the input of the amount of focal shift is detected based on detection of an input signal which is input with the movement input device.

7. The laser treatment apparatus according to claim 1, wherein the adjustment device includes a focal shift lens disposed in the light delivery optical system, a movement device which moves the focal shift lens along the optical axis of the light delivery optical system,
and a detection device which detects movement of the focal shift lens caused by the movement device, and
the input of the amount of focal shift is detected based on detection of a detection signal which is detected by the detection device and is input with the input means.

8. The laser treatment apparatus according to claim 1 further including a display device which displays a state of the focal position of the laser beam.

9. The laser treatment apparatus according to claim 8, wherein the display device displays a shift direction and a shift amount of the focal position of the laser beam with respect to the focal position of the aiming light.

10. The laser treatment apparatus according to claim 1 further including a mode selection device for selecting an operational mode of the apparatus from a standard mode and a restriction mode,
wherein the warning device provides the warning to the operator when the irradiation condition or the trigger signal is input if neither the input of the amount of focal shift nor the operation of the confirmation switch has been detected in the restriction mode selected with the mode selection device, or provides no warning to the operator when the irradiation condition or the trigger signal is input even if neither the input of the amount of focal shift nor the operation of the confirmation switch has been detected in the standard mode selected.

11. A laser treatment apparatus for treating an affected part of a patient's eye by irradiating the affected part with a laser beam, the apparatus comprising:
a laser source which emits a treatment laser beam;
light delivery optical system for delivering the laser beam emitted from the laser source to the affected part to irradiate the affected part with the laser beam;
an adjustment device including input means for inputting an amount of focal shift, which independently shifts a focal position of the laser beam in a direction of an optical axis with respect to a focal position of an aiming light based on the input amount of focal shift;
a confirmation switch which is operated by an operator when an amount of focal shift does not need to be newly input based on confirmation of a state of the focal position of the laser beam or the amount of focal shift; and
an instruction device which enables laser irradiation to the affected part when an irradiation condition of the laser beam and a trigger signal is input if input of the amount of focal shift or operation of the confirmation switch has been detected, and disables the laser irradiation when the irradiation condition or the trigger signal is input if neither the input of the amount of focal shift nor the operation of the confirmation switch has been detected.

12. The laser treatment apparatus according to claim 11 further comprising a shutter which is movable into or away from an optical path of the laser beam, wherein the instruction device controls movement of the shutter.

13. The laser treatment apparatus according to claim 11, wherein the adjustment device includes a focal shift lens disposed in the light delivery optical system,
the input means includes an operation device for moving the focal shift lens along the optical axis of the light delivery optical system, and
the input of the amount of focal shift is detected based on detection of movement of the focal shift lens or an operation signal which is input with the operation device.

14. The laser treatment apparatus according to claim 11, wherein the adjustment device includes a focal shift lens disposed in the light delivery optical system and a movement device which moves the focal shift lens along the optical axis of the light delivery optical system,
the input means includes a movement input device for inputting a movement amount of the focal shift lens to be moved by the movement device, and
the input of the amount of focal shift is detected based on detection of an input signal which is input with the movement input device.

15. The laser treatment apparatus according to claim 11, wherein the adjustment device includes a focal shift lens disposed in the light delivery optical system, a movement device which moves the focal shift lens along the optical axis of the light delivery optical system
and a detection device which detects movement of the focal shift lens caused by the movement device, and
the input of the amount of focal shift is detected based on detection of a detection signal which is detected by the detection device and is input with the input means.

16. The laser treatment apparatus according to claim 11 further including a display device which displays a state of the focal position of the laser beam.

17. The laser treatment apparatus according to claim 16, wherein the display device displays a shift direction and a shift amount of the focal position of the laser beam with respect to the focal position of the aiming light.

18. The laser treatment apparatus according to claim 11 further including a mode selection device for selecting an operational mode of the apparatus from a standard mode and a restriction mode.

* * * * *

UNITED STATES PATENT AND TRADEMARK OFFICE
CERTIFICATE OF CORRECTION

PATENT NO.    : 6,325,793 B1
DATED         : December 4, 2001
INVENTOR(S)   : Seiki Tomita It is certified that error appears in the above-identified patent and that said Letters Patent is hereby corrected as shown below:

<u>Column 8,</u>
Line 56, "is operator" should read -- is operated by an operator --.
Line 65, "input of" should read -- input if neither input of --.

Signed and Sealed this

Sixth Day of August, 2002

*Attest:*

*Attesting Officer*

JAMES E. ROGAN
*Director of the United States Patent and Trademark Office*